US00PP34677P2

(12) United States Plant Patent
Tuite

(10) Patent No.: US PP34,677 P2
(45) Date of Patent: Oct. 18, 2022

(54) ***SALVIA* PLANT NAMED 'TUCARINK'**

(50) Latin Name: *Salvia nemorosa*
Varietal Denomination: TUCARINK

(71) Applicant: Jonathan Tuite, Kings Lynn (GB)

(72) Inventor: Jonathan Tuite, Kings Lynn (GB)

( * ) Notice: Subject to any disclaimer, the term of this patent is extended or adjusted under 35 U.S.C. 154(b) by 0 days.

(21) Appl. No.: 17/519,397

(22) Filed: Nov. 4, 2021

Related U.S. Application Data

(60) Provisional application No. 63/118,007, filed on Nov. 25, 2020.

(51) Int. Cl.
*A01H 5/02* (2018.01)
*A01H 6/50* (2018.01)

(52) U.S. Cl.
USPC ..... Plt./475

(58) Field of Classification Search
USPC ..... Plt./475
See application file for complete search history.

*Primary Examiner* — Susan McCormick Ewoldt
(74) *Attorney, Agent, or Firm* — Penny J. Aguirre

(57) ABSTRACT

A new cultivar of hybrid *Salvia* plant named 'TUCARINK' that is characterized by its large flowers that are pink in color, its long flower spikes, its purple flowering stems, and its flowering spikes with long internodes.

2 Drawing Sheets

Botanical classification: *Salvia nemorosa.*
Variety denomination: 'TUCARINK'.

BACKGROUND OF THE INVENTION

The present invention relates to a new and distinct cultivar of *Salvia nemorosa* and will be referred to hereafter by its cultivar name, 'TUCARINK'. 'TUCARINK' is an herbaceous perennial grown for landscape use and for use as a container plant.

'TUCARINK' was discovered by the Inventor as a chance seedling that was growing in a garden bed in Kings Lynn, United Kingdom in August of 2018. The garden bed contained numerous different cultivars (all unpatented) and unnamed unpatented plants of *Salvia nemorosa*. The parent plants are unknown.

Asexual propagation of the new cultivar was first accomplished by the Inventor by stem cuttings in summer of 2018 in Kings Lynn, United Kingdom. Asexual propagation by stem cutting has shown that the characteristics of the new cultivar are stable and are reproduced true to type in successive generations.

SUMMARY OF THE INVENTION

The following traits have been repeatedly observed and represent the characteristics of the new cultivar. These attributes in combination distinguish 'TUCARINK' as a unique cultivar of *Salvia.*

1. 'TUCARINK' exhibits large flowers that are pink in color.
2. 'TUCARINK' exhibits long flower spikes.
3. 'TUCARINK' exhibits purple flowering stems.
4. 'TUCARINK' exhibits flowering spikes with long internodes.

Typical plants of the parent species differ from 'TUCARINK' in having flowers that are dark blue-violet in color. 'TUCARINK' can be compared to the *Salvia* cultivars 'Pink Friesland' (U.S. Plant Pat. No. 18,152), 'Pink Profusion' (U.S. Plant Pat. No. 31,435), and 'Pink Dawn' (U.S. Plant Pat. No. 26,343). All are similar to 'TUCARINK' in having pink flowers. 'Pink Friesland' differs from 'TUCARINK' in having flowering stems with much shorter internodes. 'Pink Profusion' differs from 'TUCARINK' in having shorter flowering stems that are more green in color with shorter internodes and flowers that are deeper pink in color. 'Pink Dawn' differs from 'TUCARINK' in having shorter flowering stems that are purple in color and flowers that are more violet in color and open from flower buds that are more purple in color.

STATEMENT REGARDING PRIOR DISCLOSURES BY THE INVENTOR

The Applicant asserts that no publications or advertisements relating to sales, offers for sale, or public distribution occurred more than one year prior to the effective filing date of this application. Any information about the claimed plant would have been obtained from a direct or indirect disclosure from the Inventor. The Applicant claims a prior art exemption under 35 U.S.C. 102(b)(1) for disclosure and/or sales prior to the filing date but less than one year prior to the effective filing date. Disclosures include but may not be limited to website listings by Bali-Hai Nursery, Hortweek, Kernock Plants, Plantagogo, Thompson & Morgan, Fairweathers, Crocus, RHS Plants, Shoot Gardening, Worfield Plants (facebook), Barnes Nursery, Candide Gardening, Suttons, Bluebell Cottage, Esveld, De Bloei Meesters, Graham's Garden Buddies, Stauden-Kirschenlohr, and Waitrose Garden.

BRIEF DESCRIPTION OF THE DRAWINGS

The accompanying color photographs illustrate the overall appearance and distinct characteristics of a 1-year-old plant of the new *Salvia* as grown in a garden in Kings Lynn, United Kingdom.

The photograph in FIG. 1 provides a side view of 'TUCARINK' in bloom.

Figure 1:
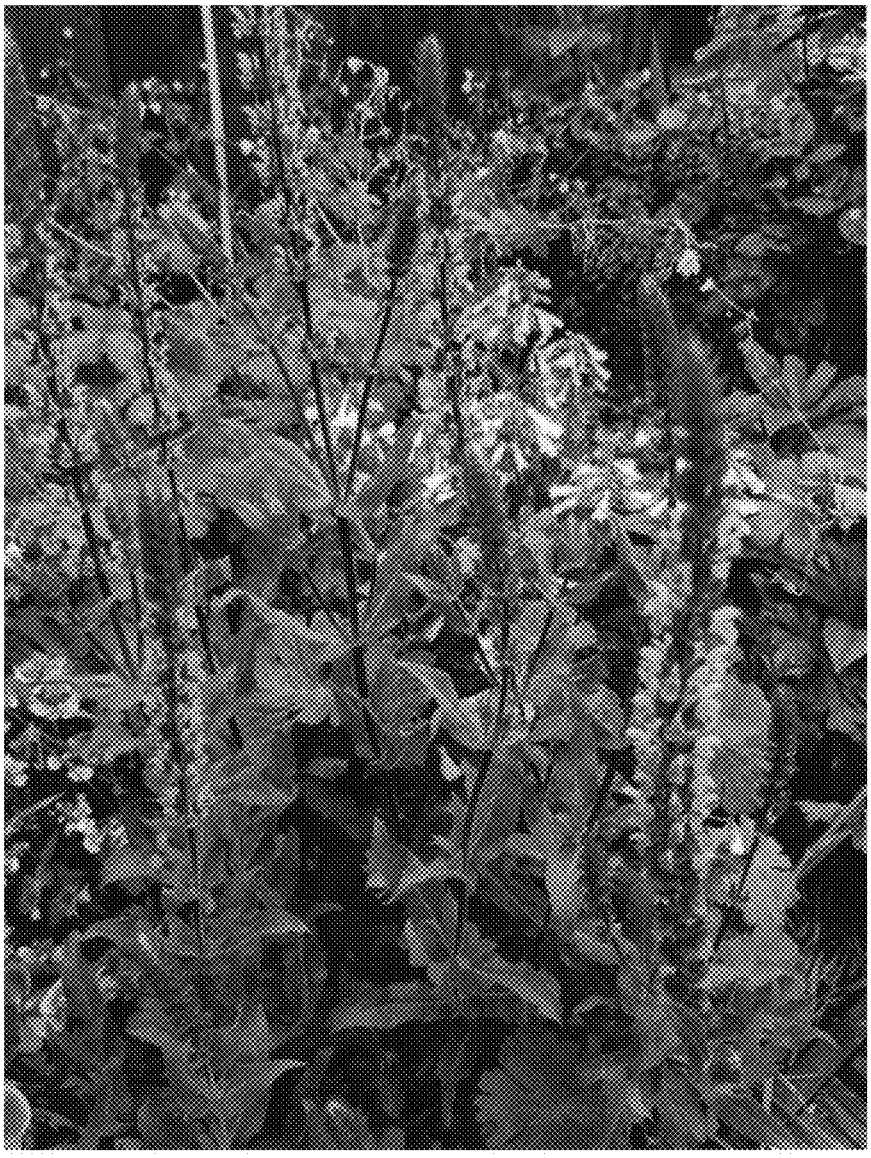
Figure 2:
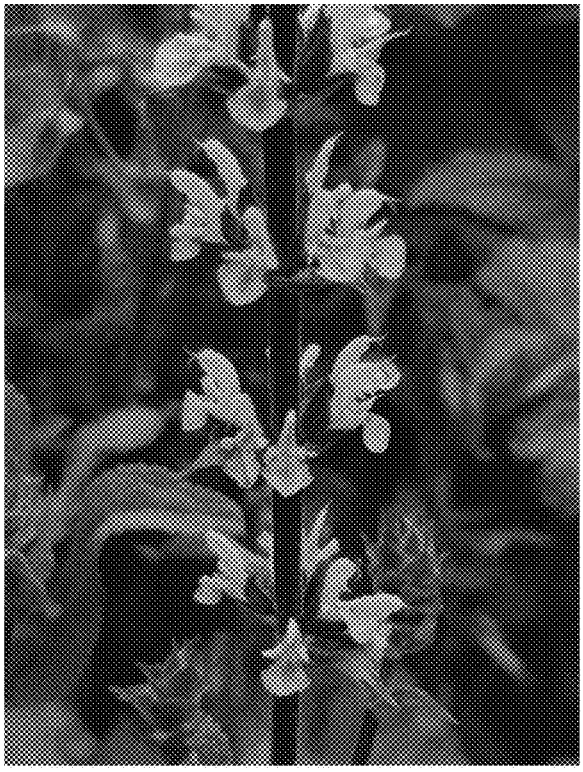

The photograph in FIG. 2 provides a close-up view of a flowering stem of 'TUCARINK'.

Figure 3:
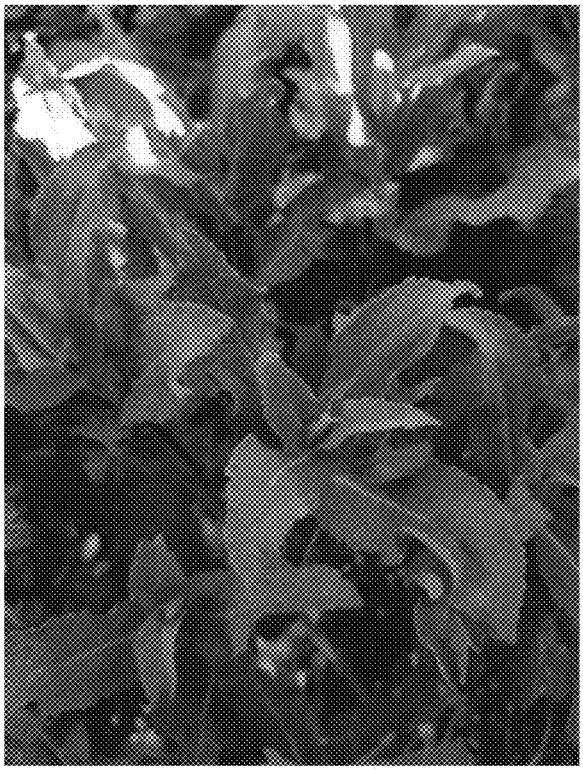

The photograph in FIG. 3 provides a close-up view of the foliage of 'TUCARINK'.

The colors in the photographs may differ slightly from the color values cited in the detailed botanical description, which accurately describe the colors of the new *Salvia*.

DETAILED BOTANICAL DESCRIPTION

The following is a detailed description of the new cultivar of 1-year-old as grown outdoors in a garden in Kings Lynn, United Kingdom. The phenotype of the new cultivar may vary with variations in environmental, climatic, and cultural conditions, as it has not been tested under all possible environmental conditions. The color determination is in accordance with The 2015 Colour Chart of The Royal Horticultural Society, London, England, except where general color terms of ordinary dictionary significance are used.

General description:

*Blooming period*.—May to late July, re-blooming from early September to early October in the United Kingdom.

*Plant type*.—Herbaceous perennial.

*Plant habit*.—Upright to spreading-upright with long flowering stems.

*Plant size*.—An average of 27.8 cm in height (soil level to top of foliar plane), 38.6 cm in height (soil level to top of floral plane), 22.9 cm in spread as a 1-year-old plant in the garden.

*Hardiness*.—At least in U.S.D.A. Zones 4 to 8.

*Diseases and pests*.—No susceptibility or resistance to diseases or pests has been observed.

*Root description*.—Fibrous.

*Propagation*.—Vegetative stem cuttings.

*Growth rate*.—Moderately vigorous.

*Root development*.—4 weeks for root initiation and about 8 weeks to produce a fully young plant.

Stem description:

*Shape*.—Quadrangular.

*Stem color*.—New growth; 144B to 144C and becoming flushed with N79A, mature stems; N79A blended at internodes with 146D and 151A.

*Stem size*.—Average of 21.3 cm in length (excluding inflorescence), 2.5 mm in diameter.

*Stem surface*.—Matte, moderately covered with short hairs, average of 0.2 mm in length, matches surface color.

*Stem fragrance*.—When rubbed, the stems are pleasantly fragrant.

*Internode length*.—Average of 3.4 cm.

*Branching*.—Average of 4 primary branches, 3 secondary branches.

Foliage description:

*Leaf shape*.—Narrowly oblong to lanceolate.

*Leaf division*.—Simple.

*Leaf base*.—Truncate.

*Leaf apex*.—Bluntly acute.

*Leaf fragrance*.—When rubbed the leaves are aromatic.

*Leaf venation*.—Pinnate, 145C in color on upper surface, 145B in color on lower surface.

*Leaf margins*.—Crenate, unlobed.

*Leaf arrangement*.—Opposite.

*Leaf attachment*.—Petiolate.

*Leaf surface*.—Both surfaces moderately rugose and matte, main vein upper surface moderately covered with very short adpressed hairs 1 mm in length, matching surface color, lower surface moderately to densely covered with very short glandular hairs an average of 1 mm in length, matching surface color.

*Leaf size*.—Up to 6.9 cm in length and 2.1 cm in width.

*Leaf color*.—Young upper surface 144A, young lower surface 146B, mature upper surface 137B, mature lower surface a blend of 138A and 147B.

*Petioles*.—Average of 1.2 cm in length, 2 mm in width at widest point, strong, color; upper surface 145A, margins 136A, lower surface 146C, both surfaces slightly glossy, both surfaces are slightly glossy and moderately to densely covered with short pubescent hairs 0.1 mm in length and matching surface color, margins moderately covered with short hairs 3 mm in length and matching leaf surface.

Inflorescence description:

*Inflorescence type*.—Terminal verticillaster.

*Lastingness of inflorescence*.—Individual flowers average of 10 days, very freely flowering, self-cleaning.

*Inflorescence size*.—An average of 10.3 cm in length and 2.3 cm in width.

*Flower type*.—Single, labiate.

*Flower number*.—An average of 92 flowers per inflorescence, quantity of flowers and buds per plant 184.

*Flower aspect*.—Outward.

*Flower fragrance*.—None.

*Flower buds*.—Obovate in shape, average of 5 mm in length and 2 mm in diameter, color; 58A, immature sepals N79B, surface is moderately pubescent with very short glandular hairs, average of 0.1 mm in length, transparent NN155D in color.

*Flower size*.—Average of 1.2 cm in length and about 6 mm in diameter, throat diameter 1 mm, tube 6 mm in length and 1.5 mm in diameter.

*Peduncle* (*rachis*).—Quadrangulate, an average of 11.7 cm in length and 2.25 mm in width, color N77A, strong, matte, surface is moderately covered with very short hairs 0.2 mm in length and too small to measure color, angles ranging between vertical and 30°.

*Pedicels*.—An average of 2 mm in length and 0.5 mm in width, color N77B, moderately strong, matte, surface is densely covered with very short hairs 0.2 mm in length, too small to measure color, held at an average angle of 45°.

*Calyx*.—Campanulate, about 5.5 mm in length and 4 mm in width.

*Sepals*.—2, oblanceolate in shape, 65% fused, 5.5 mm in length, 2 mm in width, apex emarginate, tip of sepal cleft, margins are moderately covered with very short glandular hairs; average of 2 mm in length, too small to measure color, both surfaces smooth and glabrous, matte, color; upper surface when opening and fully open 147C, veins 147A, top N77B, lower surface when opening and fully open N77B and N79B, veined N77A.

*Petals*.—Labiate, 1 upper lip, 2 lateral lobes, 1 lower lip, average of 4 per flower, 1 whorl, lower 50% fused, upper lip; 6 mm in length, 1 mm in width, obovate in shape and folded, emarginate tip, fused into tube, entire, non-undulate, upper surface glabrous, slightly velvety, matte, lower surface very slightly velvety, moderately covered with pubescent, short glandular hairs, 0.1 mm in length, transparent and NN155D in color, lateral lobes; 3 mm in length, 1 mm in width, obovate in shape, tubular, acute tip, fused into tube, entire, non-undulate, upper surface glabrous, slightly velvety, lower surface very slightly velvety, matte, moderately covered with pubescent, short glandular hairs, 0.1 mm in length, transparent and NN155D in color, lower lip; 5 mm in length, 5 mm in width, reniform, slightly concave in shape, shallow emarginate tip, fused into tube, entire, moderately undulate at the base, upper surface glabrous, slightly velvety, matte, lower surface very slightly velvety, moderately covered with pubescent, short glandular hairs, 0.1 mm in length, transparent and NN155D in color, color; when opening and fully open upper side; upper lip and lateral lobes 73D, base 68B, lower lip NN78B to NN78C, margins and top 70B, when opening and fully open lower surface; upper lip and lateral lobes 73D, base 68B, lower lip 70B, flower throat 73D, flower tube 75D.

*Floral bracts*.—Below each whorl of flowers there are two bracts, oppositely placed, broad ovate to broadly cordate in shape, 9 mm in length, 7 mm in width, broad truncate base, top cuspidate, both sides matte, smooth and glabrous, margins entire, upper surface color 72A, lower surface color 71A, moderately pubescent with very short hairs; average of 0.2 mm in length, N155A in color.

Reproductive organs:

*Gynoecium*.—Pistil; 1, average of 1 cm in length, style; 8 mm in length, 73C, base 155A, stigma; 1.25 mm in diameter, cleft, decurrent in shape, 72A in color, ovary; 160B in color.

*Androecium*.—Stamens; 2, filaments; 76A in color, average of 4 mm in length, anthers; narrow oblong, dorsifixed, 2 mm in length, 0.3 mm in width, N200A, pollen; none.

*Fruit and seed*.—Observed to be sterile with no viable seeds formed.

It is claimed:

1. A new and distinct cultivar of *Salvia* plant named 'TUCARINK' as herein illustrated and described.

* * * * *